United States Patent [19]

Drewlow

[11] Patent Number: Plant 7,241

[45] Date of Patent: Jun. 5, 1990

[54] IMPATIENS PLANT NAMED ANTARES

[75] Inventor: Lyndon W. Drewlow, Ashtabula, Ohio

[73] Assignee: Mikkelsens, Inc., Ashtabula, Ohio

[21] Appl. No.: 308,819

[22] Filed: Feb. 9, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Impatiens plant named Antares, having deep lilac flower color, compact growth habit, dense self-branching, slightly variegated leaves, early flowering, floriferous habit, and the ability to withstand both high and low temperatures.

1 Drawing Sheet

The present invention relates to a new and distinctive cultivar of Impatiens plant, botanically known as Impatiens, and known by the cultivar name Antares. Antares was developed by me through controlled breeding by crossing Mikkelsen Seedling No. 85-195-1 (seed parent) with Mikkelsen Seedling No. 85-941-3 (pollen parent). Asexual reproduction by terminal or stem cuttings has shown that the unique features of this new impatiens are stabilized and are reproduced true to type in successive propagations.

The following characteristics distinguish the new impatiens from both its parent varieties and other cultivated impatiens of this type known and used in the floriculture industry. Certain characteristics are more meaningful by reference to known cultivars. The comparison cultivars referred to are Telstar, U.S. Plant Pat. No. 4,733; Comet, U.S. Plant Pat. No. 5,920; Corona, U.S. Plant Pat. No. 5,184; and Sunregal, U.S. Plant Pat. No. 6,389.

1. Antares has deep lilac flowers that are darker in color than Telstar, Comet, and Corona, and similar in color to the deeper lilac in the bicolor flower of Sunregal.

2. Flower size of Antares is similar to Corona and Telstar, and slightly smaller than Comet and Sunregal.

3. Antares has a compact growth habit similar to Sunregal and Comet, but Antares is more densely self-branched. Both Corona and Telstar are more upright growing cultivars.

4. Antares has a bright green leaf, while Corona has dark green leaves and Comet, Telstar and Sunregal have red-green leaves, with the leaves of Sunregal being the darkest.

5. The midrib of the Antares leaf has only a trace of red tint, while Corona, Telstar, Comet and Sunregal have a red midrib, with the red even carrying into the venation.

6. Stems of new growth of Antares show only a small amount of red coloration, while the stems of the other four cultivars show heavy red coloration.

7. Internode length on Antares is much more compact than the other four cultivars thus helping to produce the compact dense growth habit.

8. The leaves of Antares are smaller than Comet and larger than Sunregal. The leaves of Corona and Telstar are similar in size but broader.

9. Spurs on flowers of Antares are similar in reddish color to Sunregal and Comet, with Corona being darker and Telstar lighter in color.

10. Flower peduncles of Antares and Sunregal have only a red tint, while Comet, Telstar and Corona all have much deeper red coloration.

11. Young flower buds are green in color, while four comparison cultivars have reddish flower buds.

12. The leaves of Antares have only a trace of cream variegation, which is similar to Corona; Telstar and Comet are more heavily variegated; and Sunregal has no variegation whatsoever.

13. Ciliate on leaves are yellowish green (cream) while the ciliate of the four comparison cultivars are red tinged.

14. Flowering is early like Comet and Sunregal, being 7 to 10 days earlier than Corona and Telstar.

15. Antares is able to withstand both high temperature and sunlight, and low temperatures (40° to 50° F.), thus extending the growing season.

16. The highly floriferous nature of Antares makes it good for 10 and 15 cm pots, and 25 cm hanging baskets.

The accompanying colored photograph is a top perspective view showing the overall appearance of Antares, with colors being as true as it is reasonably possible to obtain in a colored reproduction of this type. The photograph was taken in late June, 1988 of a plant grown in a greenhouse.

The following is a detailed description of Antares based on plants produced under commercial practices in Ashtabula, Ohio under both greenhouse and outdoor growing conditions. Color references are made to the Royal Horticultural Society Colour Chart except where general terms of ordinary dictionary significance are used.

Parentage: A controlled cross between Mikkelsen Seedling No. 85-195-1 and Mikkelsen Seedling No. 85-941-3.

Propagation:

*Type cutting.*—Stem tip 15 mm long will develop to 4 to 5 cm long in 18 to 21 days.

*Time to root.*—8 to 10 days at 23° C. summer, and 10 to 12 days at 20° C. winter.

*Rooting habit.*—Heavy, fibrous.

Plant description:

*Form.*—Symmetrically mounded, compact, self-branching flowering herb.

*Habit of growth.*—Compact, vigorous, heavy, self-branching, with flowering over the top of the foliage. Once flowering starts, it is continuous.

*Foliage.*—Bright green leaves with green venation. Under high light conditions mature foliage has an area of cream variegation around the midrib expanding two-thirds of the way up the leaf. Under low light, immature leaves will be solid green with a cream midrib. (1) Size: 7 to 9 cm in length at maturity, and 2 to 3 cm wide. Environment can affect the size of the leaf. (2) Shape: Lanceolate with acute base and apex. (3) Texture: Upper surface slightly hirsute and lower glabrous. (4) Margin: Entire and finely ciliated. (5) Color: Young foliage, top side: 137A. Under side: 137D. Mature foliage, top side: 147A. Under side: 137C. (6) Venation: pinnate, green in color.

Flowering description:

*Flowering habits.*—Flowers continuously from leaf whorl in progressively orderly manner with either 1 or 2 flowers per leaf and in about equal numbers. Whorl above starts to open about the time the first flowers in the whorl below have finished flowering. The second flowers in the lower leaf whorl open as the first flowers in the upper whorl are opening in the axils. It takes 5 to 7 days from bud to bloom and flowers last two weeks or longer.

*Natural flowering season.*—Indeterminant and continuous. Quantity of flowering increases with increasing levels of light.

*Flower buds.*—Ellipsoidal, flowers perfect. Light red spur up to 4.0 cm long on mature buds with throat behind ovary and originating from the main sepal.

*Flowers borne.*—On individual pedicels with purplish cast from whorls of 4 to 5 leaves, flowering progressively around the whorl as buds develop. Approximately 50% of leaf axils have two flowers with the remaining having one flower.

*Quantity of flowers.*—Very floriferous due to its highly self-branched habit and its leaf axils having up to two flowers. Flower development is continuous once flowering begins.

*Petals.*—(1) Shape: Heart shaped with top petal the largest. (2) Color: Top side in summer when opening, between 72C and 77B fading to slightly lighter than 77B; under side 77C. (3) Number of petals: Five (5) in number. (4) Size of flowers: 4.0 to 4.5 cm in diameter.

*Reproductive organs.*—(1) Stamens: Five (5) in number. (a) Anther shape: Hooded, color cream with reddish purple tinge. (b) Pollen color: Cream. (2) Pistils: (a) Stigma shape: Five (5) in number, segmented, column shaped; color, cream with reddish tint. (b) Style color: Cream. (c) Ovaries: Five (5) in number, size 5 mm, color, green.

Disease resistance: No significant disease or insect problems noted to date.

I claim:

1. A new and distinct cultivar of Impatiens plant named Antares, as illustrated and described.

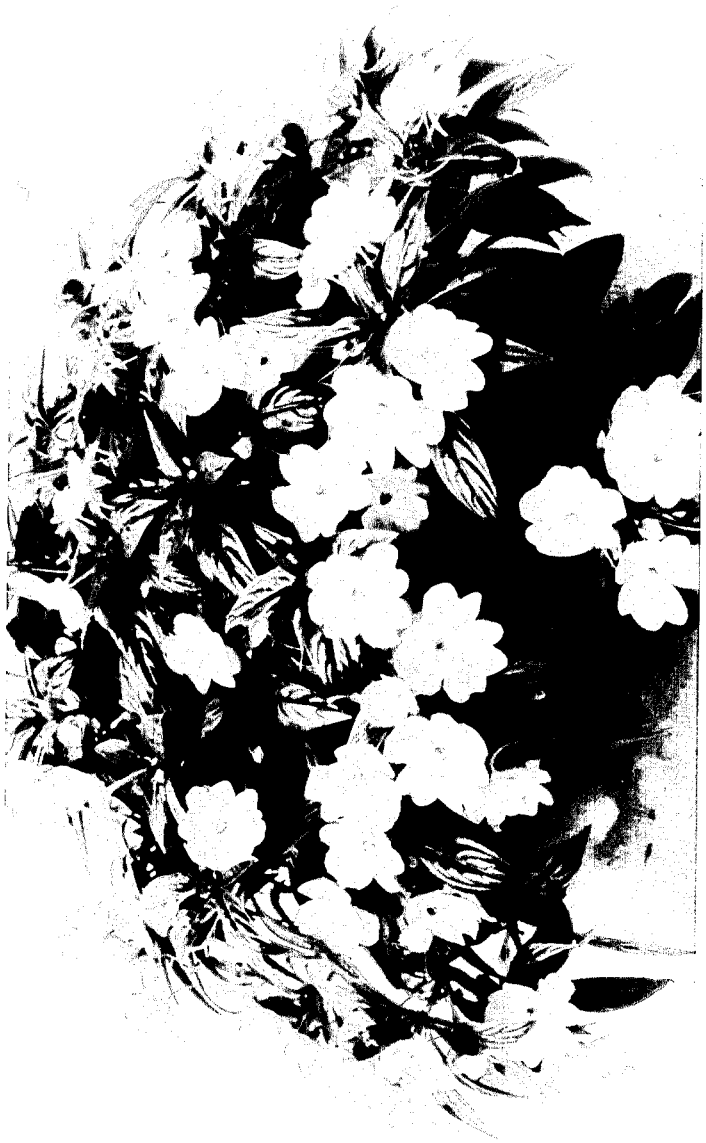

* * * * *